United States Patent [19]

Yamawaki

[11] Patent Number: 4,983,166
[45] Date of Patent: Jan. 8, 1991

[54] BALLOON CATHETER & METHOD OF USE OF THE SAME

[76] Inventor: Yoshiharu Yamawaki, 68-banchi, 7-chome, Ozakikita-machi, Kakamigahara-shi, Gifu, Japan

[21] Appl. No.: 511,917

[22] Filed: Apr. 16, 1990

Related U.S. Application Data

[63] Continuation of Ser. No. 229,677, Aug. 8, 1988, abandoned.

[30] Foreign Application Priority Data

Dec. 28, 1987 [JP] Japan .................. 62-334175

[51] Int. Cl.⁵ .................................. A61M 29/00
[52] U.S. Cl. .................... 604/96; 604/102; 604/281; 606/194
[58] Field of Search ............. 604/93, 96, 97, 98, 604/101–102, 280, 281; 600/18, 31; 606/191–197

[56] References Cited

U.S. PATENT DOCUMENTS

| | | | |
|---|---|---|---|
| 550,238 | 11/1895 | Allen | 604/102 |
| 2,642,874 | 6/1953 | Keeling | 604/102 |
| 3,736,939 | 6/1973 | Taylor | 604/96 |
| 3,977,408 | 8/1976 | MacKew | 604/102 |
| 4,276,874 | 7/1981 | Wolvek et al. | |
| 4,299,226 | 11/1981 | Banka | |
| 4,406,653 | 9/1983 | Nunez | |
| 4,631,054 | 12/1986 | Kim | 604/280 |
| 4,658,812 | 4/1987 | Hatzenbuhler et al. | 604/96 |
| 4,714,460 | 12/1987 | Calderon | 604/264 |
| 4,741,328 | 5/1988 | Gabbay | 600/18 |
| 4,762,125 | 8/1988 | Leiman et al. | 604/96 |
| 4,771,776 | 9/1988 | Powell et al. | 604/96 |
| 4,777,951 | 10/1988 | Cribier et al. | 604/96 |
| 4,790,315 | 12/1988 | Mueller, Jr. et al. | 604/96 |
| 4,917,667 | 4/1990 | Jackson | 604/96 |

FOREIGN PATENT DOCUMENTS

| | | | |
|---|---|---|---|
| 3441586 | 5/1986 | Fed. Rep. of Germany | 604/96 |
| 57-195470 | 5/1981 | Japan . | |
| 59-177064 | 3/1983 | Japan . | |

Primary Examiner—C. Fred Rosenbaum
Assistant Examiner—Kathleen A. Daley
Attorney, Agent, or Firm—Armstrong, Nikaido, Marmelstein, Kubovcik, & Murray

[57] ABSTRACT

A balloon catheter comprised a balloon catheter body, a balloon, a main passage and an auxiliary passage. The balloon is provided on the periphery of the tip portion of the catheter body to inflate for blocking a bloodstream at a desired site inside blood vessels. The auxiliary passage is provided for inflating the balloon. The main passage is provided behind the balloon, having an opening to eject a drug. The tip portion of the balloon catheter is inserted into one of branches of the blood vessel near targeted affected part. A fluid is injected into the balloon so that the balloon blocks a bloodstream in the branches. Therefore, a drug is ejected through the main passage of the balloon catheter into other branches.

4 Claims, 5 Drawing Sheets

BALLOON CATHETER & METHOD OF USE OF THE SAME

This application is a continuation of application Ser. No. 229,677 now abandoned filed Aug. 8, 1988.

BACKGROUND OF THE INVENTION

The present invention relates to a balloon catheter used in carrying out an examination or therapy of affected parts inside blood vessels and, more particularly, to a balloon catheter which is effective for use in angiography of abdominal arteries and veins and portal veins.

Generally, a catheter is a tubular device which is inserted into blood vessels, urethrae, etc. for therapy, diagnosis and the like. The catheter is provided with a balloon on the periphery of the tip portion.

This balloon catheter is usually provided with a main passage having an opening at the tip portion of a catheter body for injection of drugs such as contrast medium into blood vessels and the like and an auxiliary passage for injection of gates, liquids, etc. into the balloon to inflate it. The balloon of this balloon catheter can be used for various purpose. For instance, it can be used for dilating and expanding a stenosed or contracted portion in blood vessels or for guiding the tip of the catheter body into any desired site with the pressure of the bloodstream acting upon the balloon.

The aforementioned balloon catheter is disclosed in, for example, U.S. Pat. No. 4,299,226 and Japanese Laying-Open Gazette No. 177,064/1984. FIG. 1 shows the manner in which the balloon catheter is used and selective hepatography is carried out. FIG. 1 shows a balloon catheter 30 comprising a catheter body 31 and a balloon 32 at the tip thereof. As shown in FIG. 1, contrast medium is injected into an affected part from the main passage opening at the tip of the catheter body 31. By using the balloon catheter in this manner, small lesions (e.g. the hepatic carcinoma A shown in FIG. 1), which could not be photographed with conventional angiography, can now be detected and transcatheter arterial embolization (TAE) and transcatheter arterial infusion (TAI) can now be conducted more safely and reliably. In this context, the embolization is surgical technique in an operation for hepatic carcinoma or the like where the blood flow to the affected part of the tumor or the like is stopped by blocking the artery, resulting in necrosis of the tumor.

However, for example, the case of hepatography of the abdomen or hepatic artery embolization, the hepatic artery tends to be constricted due to repeated insertion of the catheter. Accordingly, insertion of such a balloon catheter into the hepatic artery becomes difficult, so that the injection of contrast medium and the like becomes difficult. In another case, in which the proper hepatic artery branches off from the common hepatic artery at a very sharp angle, there are some difficulties in inserting the catheter into the proper hepatic artery, whereby adequate angiography of those area is impossible.

Japanese Patent Laying-Open Gazette No. 195470/1982 discloses a balloon catheter which comprises a catheter body having a main passage and an auxiliary passage and a balloon attached to the tip of the catheter body. The opening of the main passage is provided behind the balloon. The auxiliary passage leads to the balloon.

In the balloon catheter, the balloon is provided only for guiding the tip portion of the balloon catheter in blood stream by drifting through blood vessels, not for blocking the blood vessels.

SUMMARY OF THE INVENTION

It is an object of the present invention is to provide a balloon catheter with which TAE and TAI can be performed safely and reliably, even if the blood vessels are so narrow that insertion of the catheter is difficult.

It is another object of the present invention is to provide a balloon catheter from which embolic substances can be easily removed.

It is yet another object of the present invention is to provide a method of use of the balloon catheter with which TAE and TAI can be performed safely and reliably, even if the blood vessels are so narrow that insertion of the catheter is difficult.

A balloon catheter according to the present invention comprises a balloon catheter body, a balloon, a main passage and an auxiliary passage.

The balloon is provided on the periphery of the tip portion of the catheter body to inflate for blocking the bloodstream at a desired site inside the blood vessels. The auxiliary passage is provided in the catheter body to inject a fluid into the balloon for inflating the balloon. The main passage is provided in a portion of the catheter body behind the balloon, having an opening formed on the lateral surface of the catheter body, so as to transport and eject a drug after the balloon blocks the bloodstream.

According to another aspect of the present invention, a method of use of a balloon catheter comprises the following steps of:
(a) Inserting the balloon catheter into a blood vessel with a balloon contracting.
(b) Making the tip portion of the balloon catheter drift through the blood vessel to a branch portion of the blood vessel near targeted affected part.
(c) Guiding the tip portion of the balloon catheter into one of the branches in the branch portion.
(d) Injecting a fluid into the balloon so that the balloon is inflated and blocks blood flow in the one of the branches.
(e) Then, ejecting a drug through a main passage of the balloon catheter into another of the branches.

A description will be made, as an example, of a case in which contrast medium must be injected into one of two branches of an artery extending in different directions.

Such a branch is sometimes narrow of diverges at a sharp angle, making if difficult to insert the catheter. In this case, the tip portion of the catheter is inserted from furcation into another of the branches extending in the other direction. Then, the balloon is inflated at this spot to cut off the blood flow into the latter branch. As a result, the arterial blood upstream of the furcation flows exclusively into the former branch. Because the contrast medium is injected through the main passage only to the former branch in this condition, the former branch can be photographed, allowing angiography of any desired site without inserting the catheter into the former branch. The similar result is obtained even when injecting embolic substances in which without inserting the catheter directly into the affected part, the embolic substances can be injected into any desired part with the balloon catheter.

These objects and other objects, features, aspects and advantages of the present invention will become more apparent from the following detailed description of the present invention when in conjunction with the accompanying drawings.

DESCRIPTION OF THE PREFERRED EMBODIMENTS

Embodiments of the present invention are now described in detail with reference to the accompanying drawings.

Figure 1:
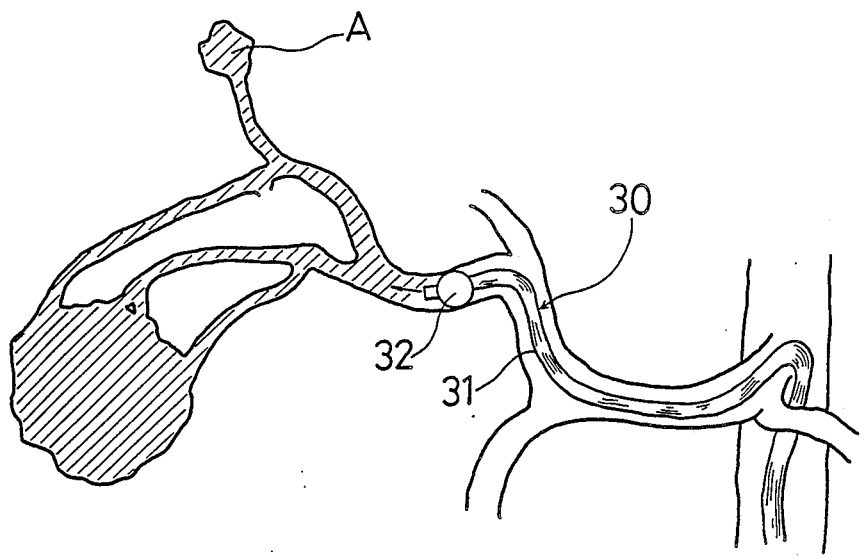
FIG. 1 is a sectional side view of a part of a human body for explaining usage of a conventional catheters.
Figure 2:
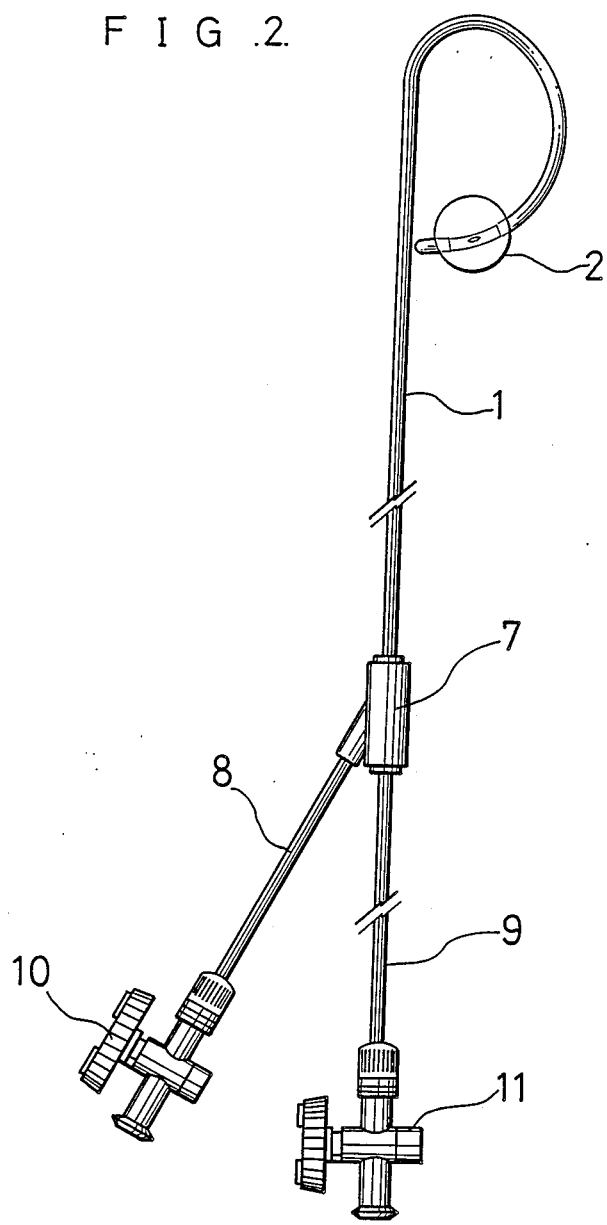
FIG. 2 is a plan view of a balloon catheter according to the present invention.
Figure 3:
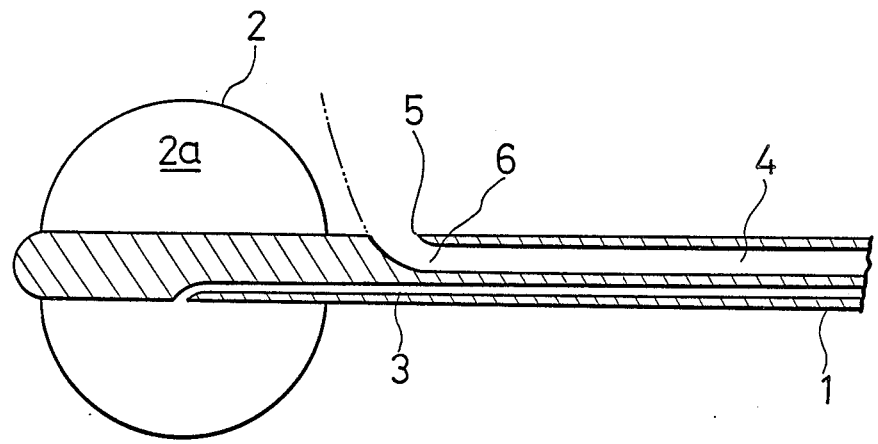
FIG. 3 is a sectional side view of the tip portion as shown in FIG. 2 with a balloon being inflated.

FIG. 2 shows a balloon catheter in accordance with one of the embodiments, and FIG. 3 shows the tip portion thereof.

Referring to FIG. 2, the tip portion of a catheter body 1 of the balloon catheter is curved like a ring. The catheter body 1 has a balloon 2 on the tip portion. The balloon 2 is made of, for example, quality natural rubber. While shown in inflating condition in FIGS. 2 and 3, the balloon 2 is shown in contracting condition in FIG. 4. An auxiliary passage 3 is provided in the catheter body 1 such that the passage 3 leads to inside 2a of the balloon 2.

In the catheter body 1, a main passage 4 is also provided for injecting drugs such as contrast medium, anticancer drugs, embolic substances, etc. into the affected part. This main passage, extending along the catheter body 1, has a lateral pore 5 opening to the outside on the periphery of the catheter body 1. The pore 5 is apart backward from the balloon by 1 to 2 cm. This means that the balloon catheter of this embodiment differs from the conventional catheters where the main passage 4 opens onto the tip, in that the tip portion of the catheter of this embodiment is a blind tube and the end surface of the tip is hemispherical. In addition, the main passage 4 is designed rot only to transport drugs such as embolic substances but also to clean the passage 4 clogged with drugs such that a flexible member (e.g. a guide wire, etc. made cf coiled stainless steel wire) can be inserted. Accordingly, a portion 6 of the main passage 4 though which a linear portion of the main passage 4 is connected to the lateral pore 5 smoothoy formed to have a curve with a large radius of curvature so as to allow ejection of embolic substances and the like contained inside the main passage 4. The curved passage 6 is designed in such a way that the tip of the flexible member does not touch the balloon 2, when the flexible member is inserted into the main passage 4.

The base end of the catheter body 1 is connected through a joint 7 to a pair of tubes 8 and 9. The tube 8, leading to the main passage 4, has at one end a valve 10 which has a port for introducing gas or liquid so as to inflate the balloon 2. The tube 9, leading to the auxiliary passage 3, has a valve 11 which has a port for introducing drags into the passage 3.

A method of use of the above balloon catheter is described in the following.

Figure 4:
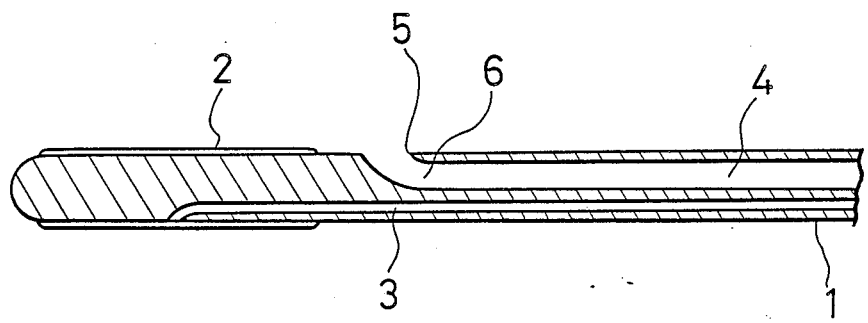
FIG. 4 is a sectional side view of the rip portion as shown in FIG. 2 with a balloon contracting.

The balloon catheter in shriveled condition as shown in FIG. 4 is first guided into the blood vessel by use of an insertion device, and the balloon catheter is then propelled to the targeted affected part along a bloodstream on the blood vessel. For example, a description is made how hepatography and embolization are performed using the balloon catheter in the following.

Figure 5:
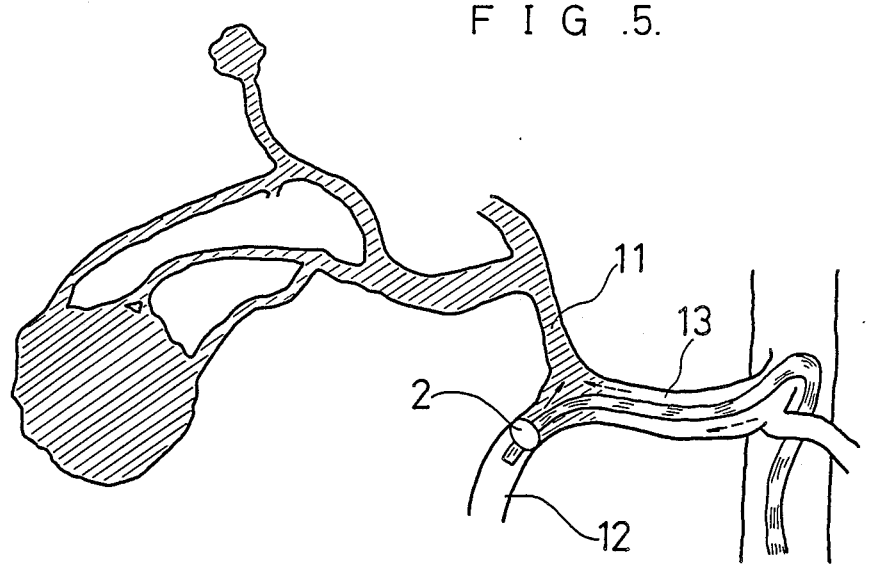
FIGS. 5, 6, 7 and 8 are respectively sectional side views of parts of a human body for explaining usage of the balloon catheter according to the present invention.

FIG. 5, for instance, shows a case where the proper hepatic artery 11 is so narrow that direct insertion of the catheter into the proper hepatic artery 11 is difficult. In this case, the tip of the catheter body 11 is first inserted into the gastroduodenal artery 12 with the balloon 2 contracting, and then gas or liquid to inflate the balloon 2 is injected through the auxiliary passage 3 of the catheter body 1 to the balloon 2. The balloon 2 is inflated, thereby blocking the blood flow of the gastroduodenal artery 12. Then, contrast mediums or embolic substances (hereinafter referred to as a contrast medium) are injected through the main passage 4 of the catheter body 1. This contrast medium is brought into the proper hepatic artery 11 with the bloodstream in the common hepatic artery 13, as arrows show. In this manner, angiography or embolization of the proper hepatic artery 11 is made. Inflation and contraction of the balloon 2 are performed with a syringe. It is advisable to use physiological saline, glucose solution, etc. that are innocuous to the human body, to inflate the balloon 2. However, in case where these liquids are difficult to recover, carbon dioxide gas, which is easy to recover, may be used instead.

Figure 6:
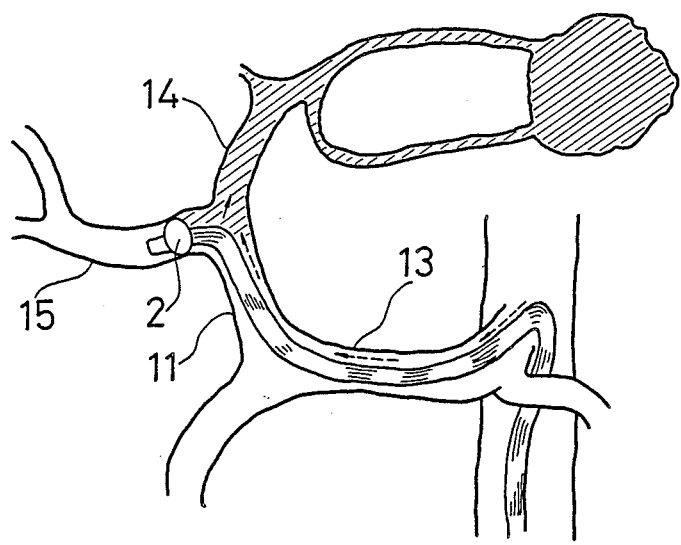

FIG. 6 shows a case where insertion of the catheter into the left hepatic artery 14 is difficult. In this case, the catheter tip is inserted into the right hepatic artery 15 and the balloon 2 is inflated to stop blood flow to the right hepatic artery. Thus, the contrast medium from the lateral pore 5 is injected into the bloodstream of the proper hepatic artery 11, and then moves into the left hepatic artery 14. As a result, angiography or embolization of the targeted affected is made.

Figure 7:
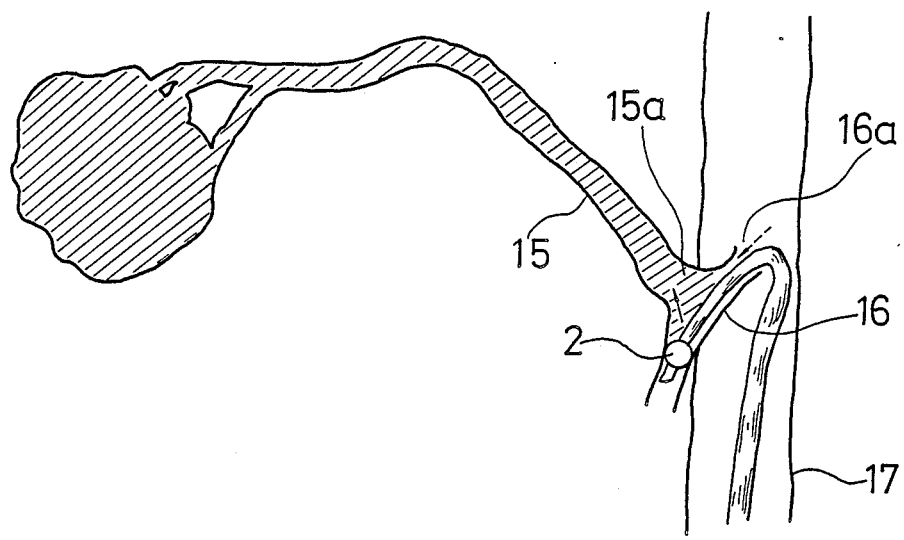

FIG. 7 shows a case of performing angiography or embolization of the right hepatic artery. Occasionally, a patient has a large distance between the furcation 16a of the superior mesenteric artery 16 and the spot 15a where the hepatic artery 15 branches off. In this case, it is difficult to directly insert the catheter into the hepatic artery 15 from the main abdominal aorta 17. Accordingly, in this case, the catheter tip is inserted into the superior mesenteric artery 16 and in the same manner as that previously mentioned, angiography or embolization is carried out using hemostasis cased by the balloon 2 and the blood flow from the superior mesenteric artery 16.

Figure 8:
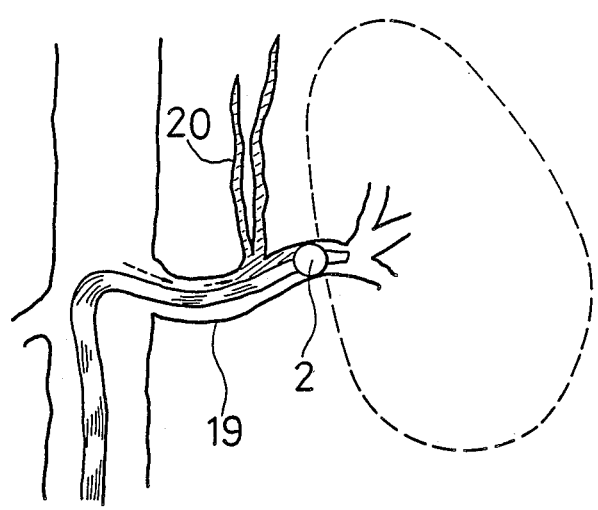

FIG. 8 shows a case of selective angiography of the inferior suprarenal artery 20 branching off from the renal artery 19. In this case, selective angiography of the proper site into which the catheter cannot be inserted, can be performed in the same manner as that previously mentioned.

As described above, because the balloon catheter comprises the balloon 2 for hemostasis, the main passage 4 and the lateral pore 5 for injection of drugs and the like behind the balloon 2, whereby arterial embolization, injection of drugs, etc. can be safely and reliably performed, even when the catheter cannot be directly inserted into the targeted affected part.

Meanwhile, embolic substances may clog the main passage 4. However, since in the above embodiment a linear portion of the main passage 4 and the lateral pore 5 are smoothly connected with each other through the curved passage 6, a ejection member such as a guide wire can be inserted in the main passage 4 smoothly and the embolic substances clogging the main passage 4 are smoothly ejected to the outside. In this case, although the ejection member may protrude from the lateral pore 5 to the outside, as shown with a phantom line in FIG. 3, the curved passage 6 is designed in such a way that the tip of the guide wire and the like protruded does not touch the balloon 2, whereby the balloon 2 cannot be ruptured by the guide wire and the like in the process of ejecting the embolic substances. Furthermore, since the curved passage 6 is provided, when the guide wire and the like is protruded to the outside or pulled back into the main passage 4, the guide wire and the like cannot be trapped in a portion near the lateral pore 5, allowing smooth operation.

Since the main passage 4 is formed as mentioned above, a thinner catheter which is capable of being inserted into the main passage 4 can be used. The thinner catheter may have a balloon or no balloon.

In the aforementioned embodiment, the balloon catheter is used in hepatography or cmbolization, but it can be used for various medical treatments for affected parts into which the conventional catheter cannot be directly inserted.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A balloon catheter for injecting a drug to an affected part through an artery, comprising:

a catheter body having a circulatory curved tip end portion, whereby said tip end portion can be inserted from a thicker artery into a thinner artery diverging from said thicker artery at an acute angle;

a main passage provided in said catheter body for transporting and ejecting said drug, said main passage having an opening formed on a peripheral surface of said curved tip end portion and a curved portion smoothly curved toward said opening whereby a drug ejecting member and a thinner catheter are allowed to go through said main passage;

a balloon provided around the periphery in said curved tip end portion between said tip end and said main passage, for inflating to block a bloodstream at a desired site inside said thinner artery; and an auxiliary passage provided in said catheter body for injecting fluid into said balloon for inflating said balloon.

2. A balloon catheter according to claim 1 wherein said opening is provided about 1 to 2 cm behind said balloon.

3. A balloon catheter according to claim 2, wherein the tip end of said catheter body is formed into a hemisphere shape.

4. A balloon catheter according to claim 1, further comprising a pair of tubes each having valves and are connected to said catheter body and lead to said main passage and said auxiliary passage, respectively.

* * * * *